United States Patent
Yamamoto et al.

(10) Patent No.: US 11,525,722 B2
(45) Date of Patent: Dec. 13, 2022

(54) DETECTION DEVICE

(71) Applicant: OMRON Corporation, Kyoto (JP)

(72) Inventors: Katsuyuki Yamamoto, Kusatsu (JP); Naotsugu Ueda, Funabashi (JP); Yoshiteru Kono, Higashi-Ohmi (JP)

(73) Assignee: OMRON CORPORATION, Kyoto (JP)

( * ) Notice: Subject to any disclaimer, the term of this patent is extended or adjusted under 35 U.S.C. 154(b) by 185 days.

(21) Appl. No.: 16/963,447

(22) PCT Filed: Jan. 18, 2019

(86) PCT No.: PCT/JP2019/001507
§ 371 (c)(1),
(2) Date: Jul. 20, 2020

(87) PCT Pub. No.: WO2019/163350
PCT Pub. Date: Aug. 29, 2019

(65) Prior Publication Data
US 2020/0400474 A1 Dec. 24, 2020

(30) Foreign Application Priority Data
Feb. 20, 2018 (JP) .............................. JP2018-028089

(51) Int. Cl.
*G01F 1/696* (2006.01)
*G01F 1/69* (2006.01)
(Continued)

(52) U.S. Cl.
CPC ............ *G01F 1/6965* (2013.01); *G01F 1/206* (2013.01); *G01F 1/69* (2013.01); *G01F 1/74* (2013.01);
(Continued)

(58) Field of Classification Search
None
See application file for complete search history.

(56) References Cited

U.S. PATENT DOCUMENTS

| 5,852,238 A | 12/1998 | Vaitkus |
| 6,647,777 B1 | 11/2003 | Kotaka et al. |
(Continued)

FOREIGN PATENT DOCUMENTS

| CN | 1276059 A | 12/2000 |
| CN | 1902466 A | 1/2007 |
(Continued)

OTHER PUBLICATIONS

Chinese Office Action dated Aug. 18, 2021 for the counterpart Chinese patent application.
(Continued)

*Primary Examiner* — Matthew G Marini
(74) *Attorney, Agent, or Firm* — Metrolex IP Law Group, PLLC

(57) ABSTRACT

A detection device for detecting characteristics of a mixed fluid containing different types of substances with different thermal properties within a prescribed range, includes: one or a plurality of heaters for heating the mixed fluid; a plurality of temperature detectors for detecting the temperature of the mixed fluid heated; a flow rate calculation unit for calculating the flow rate of the mixed fluid using the output from at least a portion of the plurality of temperature detectors; a correspondence relation storage unit that stores the correspondence relation between the output from the temperature detectors for a prescribed flow rate and the mixture ratio of the substances in the mixed fluid; and a mixture ratio calculation unit for calculating the mixture
(Continued)

ratio of the substances in the mixed fluid on the basis of the output from the temperature detectors and the correspondence relation.

18 Claims, 16 Drawing Sheets

(51) Int. Cl.
  *G01F 1/74* (2006.01)
  *G01N 25/18* (2006.01)
  *G01N 33/00* (2006.01)
  *G01F 1/20* (2006.01)

(52) U.S. Cl.
  CPC ......... *G01N 25/18* (2013.01); *G01N 33/0027* (2013.01)

(56) References Cited

U.S. PATENT DOCUMENTS

| | | |
|---|---|---|
| 6,871,537 B1 | 3/2005 | Gehman et al. |
| 2002/0121137 A1 | 9/2002 | Fujiwara et al. |
| 2015/0192441 A1 | 7/2015 | Tokuyasu et al. |
| 2016/0131511 A1 | 5/2016 | Shirai et al. |
| 2016/0161951 A1* | 6/2016 | Hornung ............ G01N 33/0027 73/25.03 |
| 2018/0180455 A1 | 6/2018 | Nakao et al. |

FOREIGN PATENT DOCUMENTS

| | | |
|---|---|---|
| CN | 104364619 A | 2/2015 |
| CN | 105283737 A | 1/2016 |
| JP | S56-80178 A | 7/1981 |
| JP | 2002-136595 A | 5/2002 |
| JP | 2002136595 A * | 5/2002 |
| JP | 2004-154216 A | 6/2004 |
| JP | 3658321 B2 | 6/2005 |
| JP | 2017-129470 A | 7/2017 |
| WO | 2015029890 A1 | 3/2015 |
| WO | WO-2016068725 A1 * | 5/2016 ........ A61M 16/0051 |

OTHER PUBLICATIONS

English translation of the International Search Report ("ISR") of PCT/JP2019/001507 dated Feb. 12, 2019.
Written Opinion("WO") of PCT/JP2019/001507 dated Feb. 12, 2019.
International Preliminary Report on Patentability ("IPRP") dated Jan. 28, 2020.

* cited by examiner

FIG. 7

Flow Rate A

| Output from Thermopile 7A | Mixture Ratio (Oxygen : Nitrogen) |
|---|---|
| 27000 | $\alpha 1 : \beta 1$ |
| 27100 | $\alpha 2 : \beta 2$ |
| 27200 | $\alpha 3 : \beta 3$ |
| 27300 | $\alpha 4 : \beta 4$ |

Flow Rate B

| Output from Thermopile 7A | Mixture Ratio (Oxygen : Nitrogen) |
|---|---|
| 27000 | $\alpha 5 : \beta 5$ |
| 27100 | $\alpha 6 : \beta 6$ |
| 27200 | $\alpha 7 : \beta 7$ |
| 27300 | $\alpha 8 : \beta 8$ |

Flow Rate C

DETECTION DEVICE

FIELD

The present invention relates to a detection device.

BACKGROUND

An oxygen concentrator, for instance, allows a mixed gas consisting of oxygen and nitrogen to flow in a flow path in the oxygen concentrator. When the oxygen concentrator degrades over time, the proportion of oxygen in the mixed gas decreases, while the proportion of nitrogen increases. That is, a malfunction of the oxygen concentrator can be found if the flow rate of a mixed gas and the concentration of oxygen contained in the mixed gas can be detected. Beyond the above example, there is a demand for the ability to detect the flow rate of a mixed fluid that flows in a flow path and the concentration of a substance contained in the mixed fluid. Further, Patent Document 1 discloses an invention pertaining to a thermal flow sensor.

RELATED ART DOCUMENTS

Patent Documents

Patent Document 1

Japanese Patent Number 3658321

SUMMARY

Technical Problem

Patent Document 1 discloses that when a thermal flow sensor is provided on a flow path along which a fluid flows, thermopiles provided to the thermal flow sensor detect temperature distribution information in the flow path and that a fluid flow rate can be calculated on the basis of the temperature distribution information. However, Patent Document 1 does not disclose calculating the concentration of a substance contained in a fluid on the basis of temperature distribution information when the fluid is a mixed fluid. That is, the present inventors found that to calculate the flow rate of a mixed fluid as well as the concentration of a substance contained in the mixed fluid, a concentration detection device is required separately from a thermal flow sensor, thereby increasing costs.

The present invention, in one aspect, is made in view of such circumstances, and the purpose thereof is to calculate the flow rate of a mixed fluid and the concentration of a substance contained in the mixed fluid using one detection device, thereby providing techniques to reduce the cost of detection.

Solution to Problem

The present invention adopts the following configurations to solve the problems described above.

According to one aspect of the present invention, a detection device detects the characteristics of a mixed fluid containing different types of substances with different thermal properties within a prescribed range, the detection device comprising: one or a plurality of heaters for heating the mixed fluid; a plurality of temperature detectors for detecting the temperature of the mixed fluid heated; a flow rate calculation unit for calculating the flow rate of the mixed fluid using the output from at least a portion of the plurality of temperature detectors, the flow rate calculation unit including the heater and at least a portion of the plurality of temperature detectors; a correspondence relation storage unit that stores a correspondence relation between the output from the temperature detectors for a prescribed flow rate and the mixture ratio of the substances in the mixed fluid; and a mixture ratio calculation unit for calculating the mixture ratio of the substances in the mixed fluid on the basis of the output from the temperature detectors and the correspondence relation.

Here, the prescribed range is defined as a range in which the thermal properties of the entire mixed fluid remain substantially the same even when the mixture ratio changes, for example, the range which contains the difference between the thermal resistivity (49192 $[s/m^2]$) of oxygen and the thermal resistivity (49575 $[s/m^2]$) of nitrogen. Further, the prescribed range may be defined as a range in which at least any one of the differences in thermal properties of, for example, the thermal resistivity, thermal resistance, thermal conductivity, thermal conductance, and thermal diffusivity is 1% or less with respect to the maximum value of the thermal properties of a substance contained in the mixed fluid.

The flow rate of a mixed fluid may be calculated in the above configuration with the mixed fluid heated by a heater when the mixed fluid is flowing. Further, the configuration allows for using a correspondence relation stored in a correspondence relation storage unit to calculate the mixture ratio corresponding to the output from a temperature detector. Therefore, the concentration of a substance contained in the mixed fluid can be calculated from the calculated flow rate and the mixture ratio.

According to the above aspect, the mixture ratio calculation unit in the detection device may calculate the mixture ratio of the substance in the mixed fluid on the basis of the output from the temperature detectors that constitute the flow rate calculation unit and the correspondence relation. According to said configuration, the flow rate of the mixed fluid and the concentration of a substance included in the mixed fluid may be obtained using a single detection device, thereby reducing costs.

According to the above aspect, the detection device uses the output from the temperature detectors which do not constitute the flow rate calculation unit and which are provided side by side in a direction different from the direction in which the mixed fluid flows to calculate a physical property of the mixed fluid; the mixture ratio calculation unit may calculate the mixture ratio of the substances in the mixed fluid on the basis of the output from the temperature detectors used to calculate the physical property and the correspondence relation.

According to said configuration, the output from the temperature detectors provided side by side in a direction different from the direction in which the mixed fluid flows is not affected by the flow rate. Therefore, a physical property and a mixture ratio may be calculated without depending on a flow rate. That is, a physical property and a mixture ratio may be calculated easily and accurately.

According to the above aspect, the detection device may be further provided with a flow rate correction unit for correcting the flow rate of the mixed fluid on the basis of the output from the temperature detectors used to calculate the physical property.

According to said configuration, the physical property may be used to correct the flow rate and thereby a flow rate may be calculated that approaches the flow rate of the mixed fluid that is actually flowing.

The different types of substances in the detection device according to the above aspect may be oxygen and nitrogen. According to said configuration the flow rate of a mixed fluid and the mixture ratio between oxygen and nitrogen contained in the mixed fluid may be calculated. As a matter of course, a concentration may be calculated from the flow rate and mixture ratio calculated. Further, a single device may be used to detect the concentration of oxygen in the mixed fluid when the mixture ratio calculation unit calculates the mixture ratio of the mixed fluid using the output from the temperature detectors that constitute the flow rate calculation unit.

According to the above aspect, the detection device may be further provided with a breath detection means. According to said configuration, the breath may be detected as well as the flow rate of a mixed fluid and the concentration of a substance contained in the mixed fluid.

According to the above aspect, the breath detection means in the detection device may be provided with a pressure detection device for detecting the pressure of the mixed fluid. According to said configuration, not only can the flow rate of a mixed fluid and the concentration of a substance contained in the mixed fluid be detected, but the pressure of the mixed fluid may also be detected for breath detection.

According to the above aspect, the breath detection means in the detection device may be provided with a flow rate fluctuation calculation unit for calculating the fluctuation in the flow rate of the mixed fluid on the basis of the flow rate of the mixed fluid calculated by the flow rate calculation unit.

According to said configuration the fluctuation in the flow rate of the mixed fluid may be calculated on the basis of the flow rate calculated for the mixed fluid, to thereby perform breath detection. Therefore, the breath may be detected without the need to increase the number of parts, thereby saving costs.

Effects

The present invention allows the flow rate of a mixed fluid and the concentration of a substance contained in the mixed fluid to be calculated using a single detection device, and thereby provides the technology to reduce costs required for detection.

BRIEF DESCRIPTION OF THE DRAWINGS

FIG. 7 schematically illustrates an example of a correspondence relation table;

DETAILED DESCRIPTION

Hereinafter, an embodiment according to an aspect of the present invention (hereinafter, also referred to as "the present embodiment") is described with reference to the drawings. However, the present embodiment described below is merely an example of the present invention in all respects. It goes without saying that various modifications and variations are possible without departing from the scope of the invention. That is, specific configurations may be adopted as appropriate in accordance with the embodiment when implementing the invention.

1. Example Application

Figure 1:
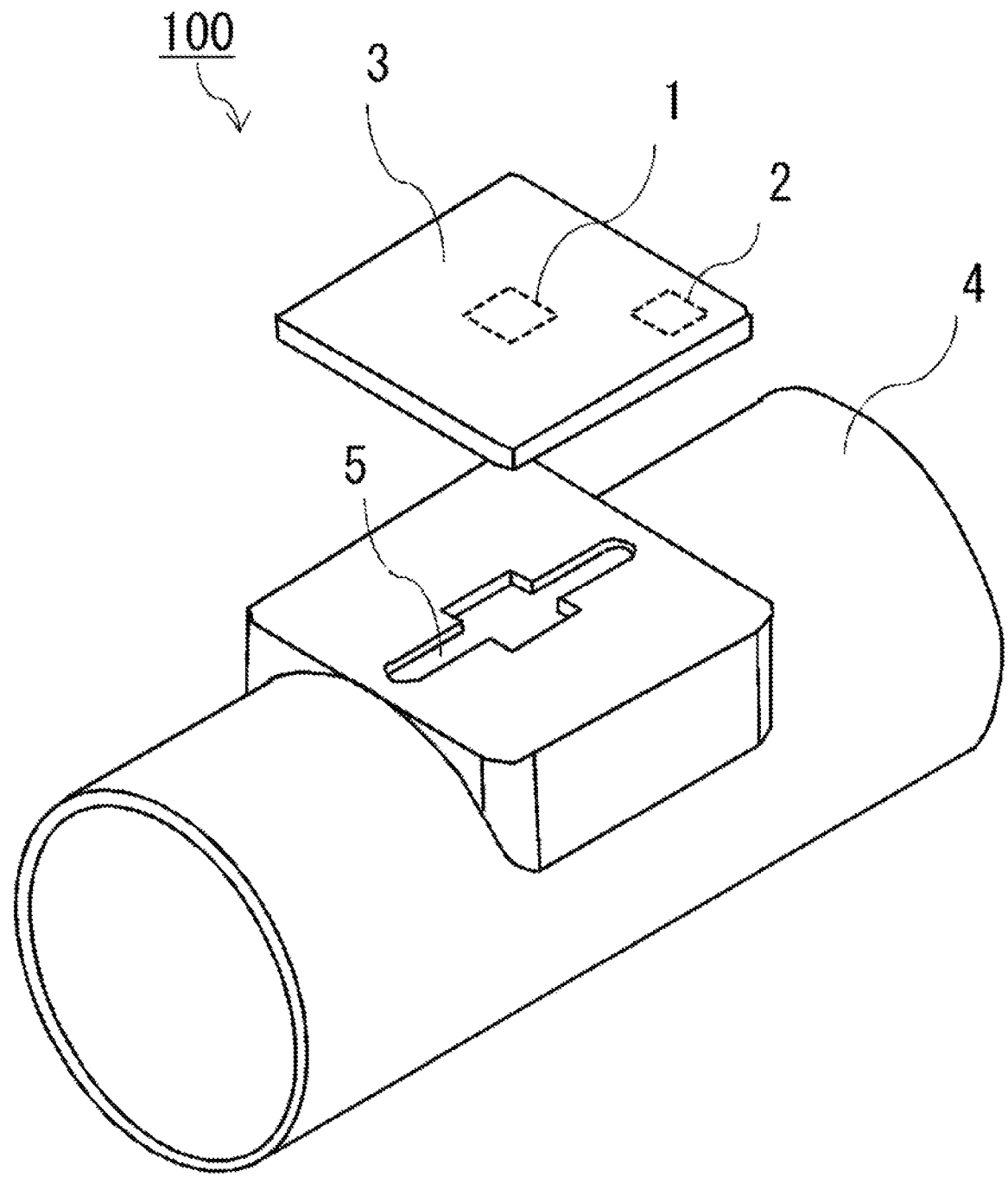
FIG. 1 schematically illustrates an example of a detection device according to an embodiment.

An example of a situation in which the present invention may be applied is described with reference to FIG. 1. FIG. 1 schematically illustrates an example of a detection device 100 according to the present embodiment. The detection device 100 is provided with a detection element 1, a control unit 2, and a circuit board 3 whereon the detection element 1 and the control unit 2 are mounted. A flow tube 4 allows a mixed fluid to flow therethrough. A single flow path section 5 is formed on the top of the flow tube 4. The detection device 100 is fixed to the flow tube 4 so that the detection element 1 is located in the flow path section 5. The detection element 1 is provided with a microheater and thermopiles near the microheater. The detection element 1 is a so-called thermal flow sensor.

Here, the flow rate of a mixed fluid is calculated as described below. When a microheater is activated with a mixed fluid flowing in a flow tube 4, the vicinity of the microheater is heated. A thermopile outputs a signal associated with the temperature near the microheater. When the microheater emits heat in the midst of the flow of the mixed fluid, the heat from the microheater is diffused unevenly under the influence of the flow of the mixed fluid. This biased diffusion is measured by the thermopiles so that the flow rate of the mixed fluid can be calculated.

Further, the concentration of a substance contained in the mixed fluid can be calculated as described below. First, a user preliminarily prepares the correspondence relation between the output from one of the thermopiles and the mixture ratio of a mixed fluid at a prescribed flow rate. Then, the user flows a fluid to be measured in the flow tube 4 so that a mixture ratio is calculated from the output value from one of the thermopiles, a flow rate calculated from the difference between the output values of the two thermopiles, and the above-described correspondence relation. The concentration of a substance contained in the mixed fluid is then calculated from the mixture ratio and the flow rate calculated.

As described above, the present embodiment allows the flow rate of a mixed fluid and the concentration of a substance contained in the mixed fluid to be detected using a single detection device 100. Therefore, the present embodiment can decrease the number of parts, thereby reducing the costs required for detection.

2. Example Configuration

Hardware Configuration

Next, an example of the detection device according to the present embodiment is described. The detection device 100 according to the present embodiment detects the flow rate and the oxygen concentration of a mixed gas consisting of oxygen and nitrogen that flows in the flow tube 4 in an oxygen concentrator; the oxygen concentrator may be used by a patient with a respiratory illness. As shown in FIG. 1, the detection device 100 is provided with a detection element 1, a control unit 2, and a circuit board 3 whereon the detection element 1 and the control unit 2 are mounted.

Figure 2:
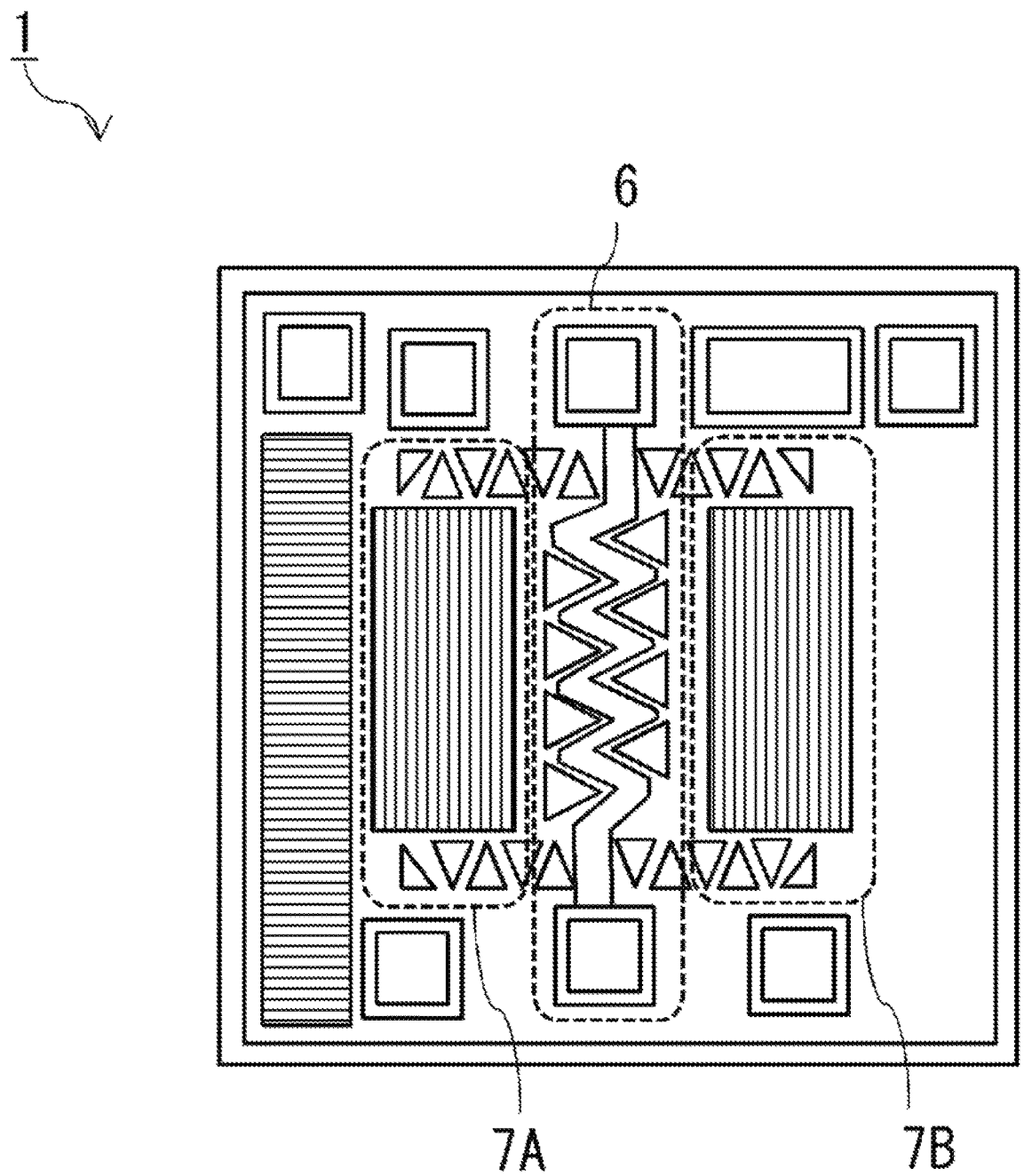
FIG. 2 is an enlarged view schematically illustrating an example of a detection element.

FIG. 2 is an enlarged view schematically illustrating an example of a detection element 1 according to the present embodiment. The detection element 1 is provided with a microheater 6 and thermopiles 7A, 7B. Here, the microheater 6 is an example of "a heater" according to the present invention. The thermopiles 7A, 7B are examples of "temperature detectors" according to the present invention. The microheater 6 is a resistor made up of, for example, polysilicon and is provided at the center portion of the detection element 1. The thermopiles 7A, 7B are provided on both sides of the microheater 6 with the microheater 6 sandwiched therebetween.

Figure 3:
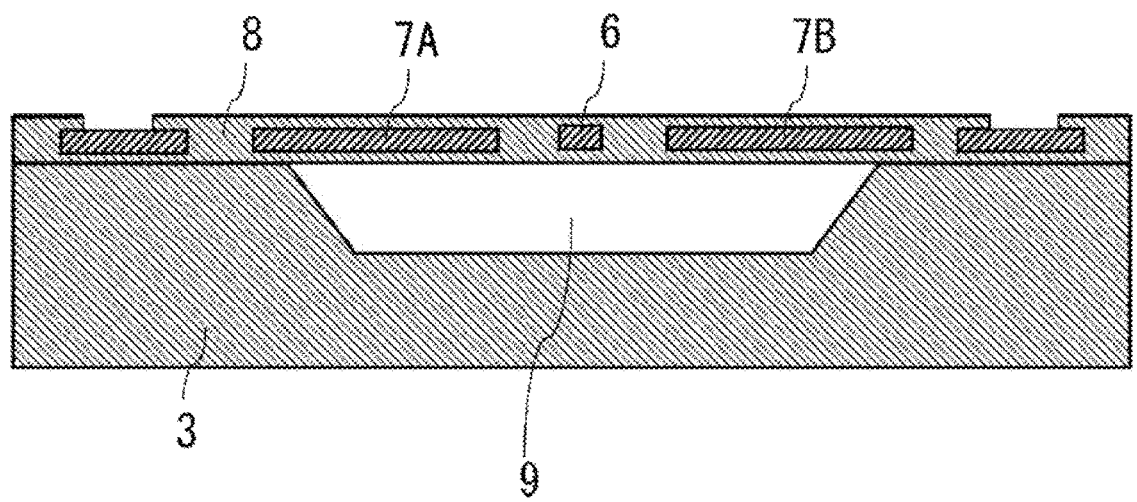
FIG. 3 schematically illustrates an example of a cross-section of a detection device according to an embodiment.
Figure 4:
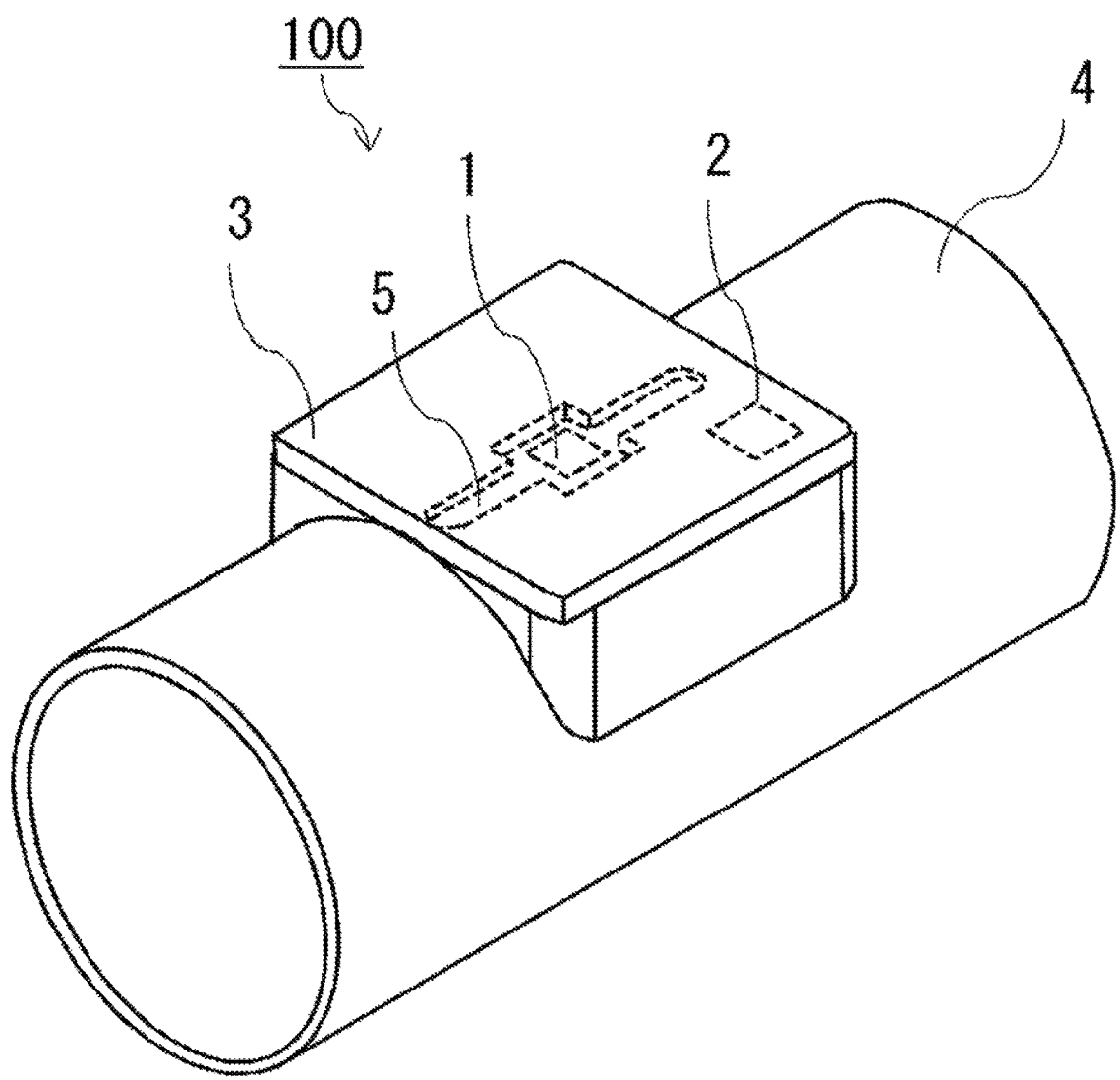
FIG. 4 is a schematic view outlining a detection device mounted on a flow tube according to an embodiment.

FIG. 3 schematically illustrates an example of the cross-section of the detection device 100. An insulating thin film 8 is formed above and below the microheater 6 and the thermopiles 7A, 7B. A cavity 9 is provided in the circuit board 3 below the thermopiles 7A, 7B. FIG. 4 is a schematic view outlining a detection device 100 mounted on a flow tube 4. The detection device 100 is mounted so that the detection element 1 fits into the center portion of the flow path section 5. Further, the detection device 100 is mounted so that the thermopile 7A is located upstream and the thermopile 7B is located downstream along the flow direction of a mixed gas.

Flow Rate Detection Principle

Figure 5A:
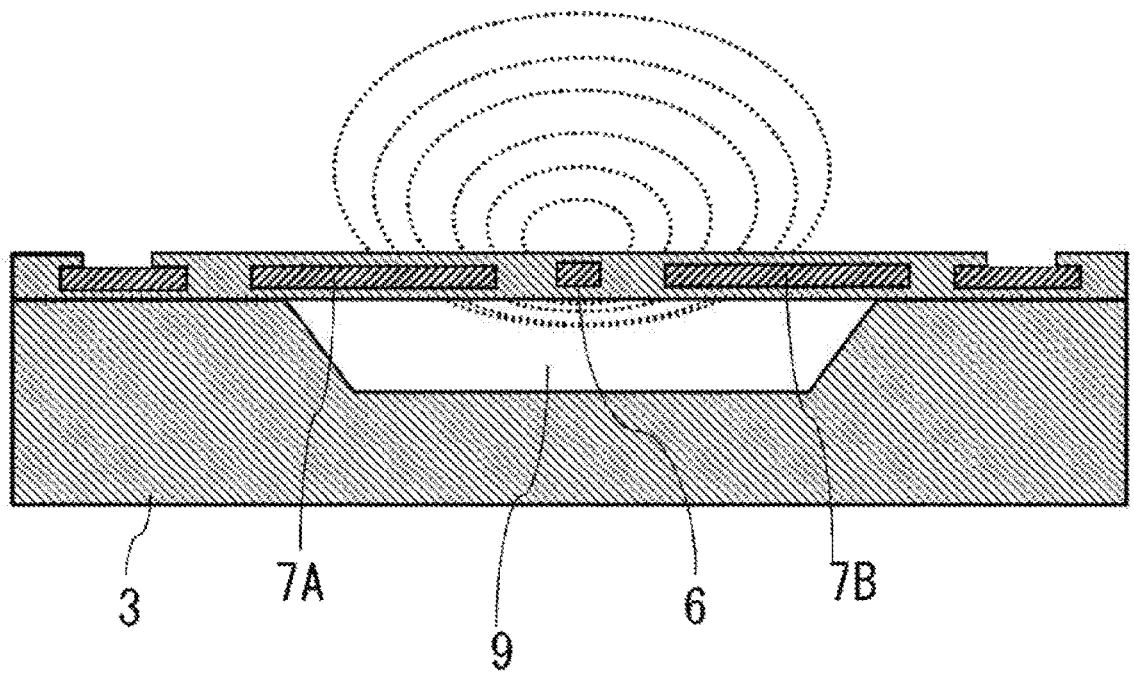
FIG. 5A schematically illustrates an example of a temperature distribution when a microheater is activated with no gas flowing in a flow tube.
Figure 5B:
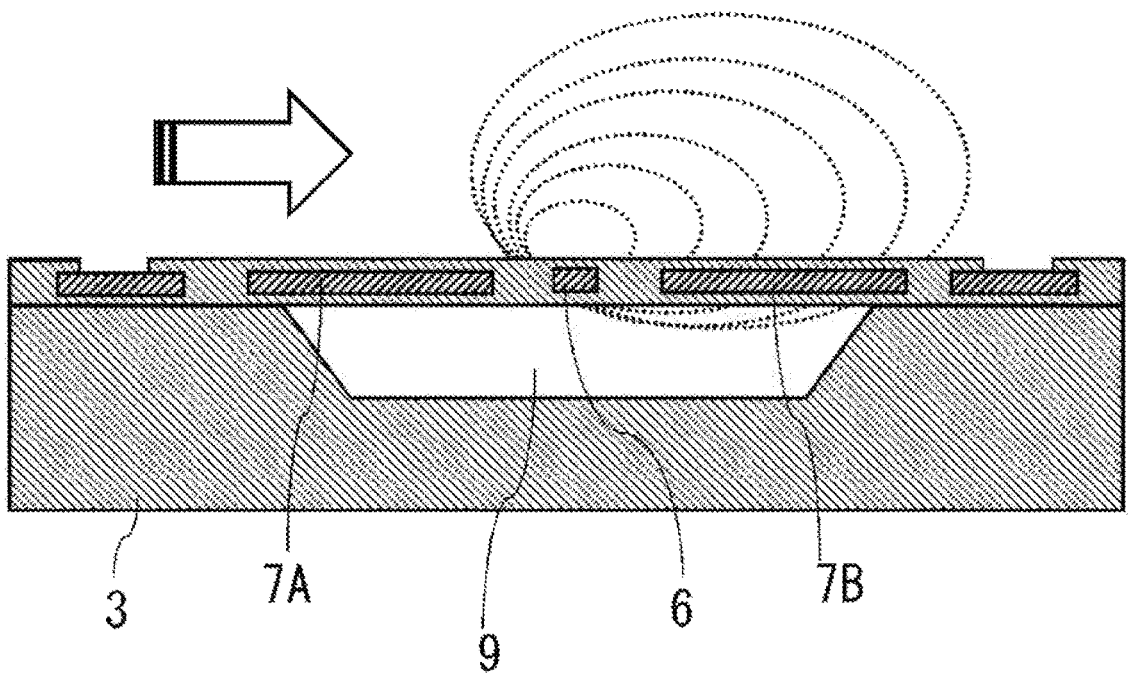
FIG. 5B schematically illustrates an example of a temperature distribution when a microheater is activated with a gas flowing in a flow tube.

Next, the principle of flow rate detection using the detection element 1 is described. FIG. 5A schematically illustrates an example of a temperature distribution when the microheater 6 is activated with no gas flowing in the flow tube 4. FIG. 5B schematically illustrates an example of a temperature distribution when the microheater 6 is activated with a gas flowing in the flow tube 4. When no gas flows in the flow tube 4, heat emitted from the microheater 6 diffuses symmetrically about the microheater 6. Therefore, there is no difference in the output from the thermopiles 7A, 7B. Whereas, when a gas flows in the flow tube 4, the heat from the microheater 6 is affected by the gas flow and significantly diffuses toward the thermopile 7B that is downstream without spreading symmetrically about the microheater 6. This causes the difference between the outputs from the thermopiles 7A, 7B. As the gas flow rate increases, the difference in the output increases. The relationship between the gas flow rate and the difference in output from the thermopiles 7A, 7B is represented by, for example, the expression (1) below:

$$\Delta V = A \cdot (T_B - T_A)^b \sqrt{v_f} \tag{1}$$

Where, $\Delta V$ represents the flow rate of a fluid; $T_A$ represents the output value from the thermopile 7A; and $T_B$ represents the output value measured by the thermopile 7B. In addition, of represents the flow velocity of a fluid; and A and b are constants. According to the present embodiment, a flow rate is calculated in accordance with the principle described above.

Functional Configuration

Figure 6:
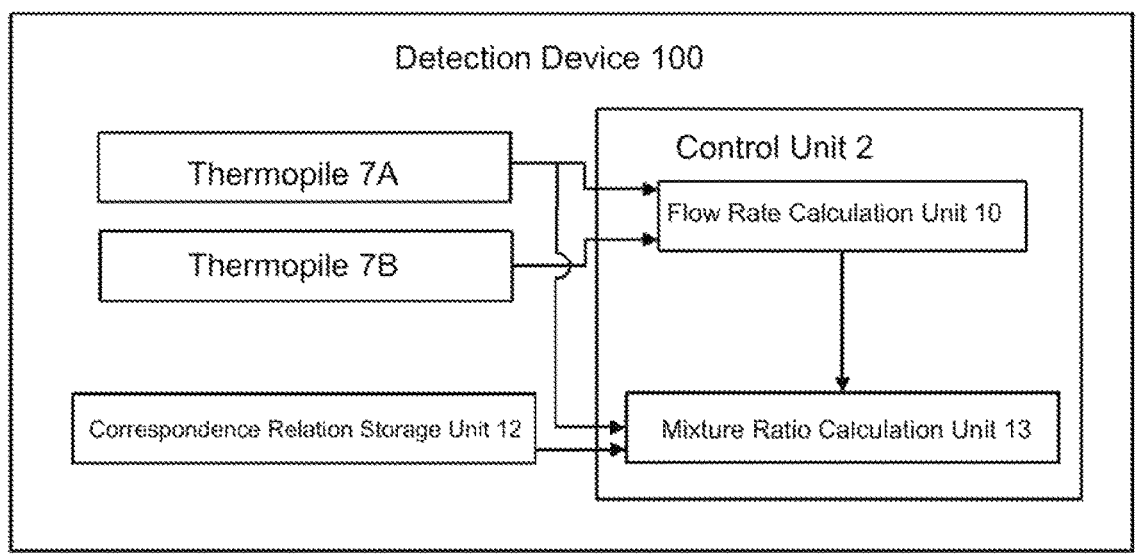
FIG. 6 is a block diagram schematically illustrating an example of a functional configuration of a detection device according to an embodiment.

FIG. 6 is a block diagram schematically illustrating an example of the functional configuration of a detection device 100. Here, the control unit 2 is provided with a flow rate calculation unit 10 that receives a signal output from the thermopiles 7A, 7B and calculates the flow rate of a fluid from the signal received. The flow rate calculation unit 10 is an example of a "flow rate calculation unit" according to the present invention. The output from the thermopiles 7A, 7B is used in the expression (1) to calculate the flow rate of a mixed gas. The control unit 2 calculates the flow rate of the mixed gas on the basis of the difference in the output from the thermopiles 7A, 7B in accordance with the expression (1).

The detection unit 100 is also provided with a correspondence relation storage unit 12 for storing a correspondence relation table 11 that indicates the correspondence relation between the output from the thermopile 7A in a prescribed flow rate and the mixture ratio of a mixed gas. FIG. 7 schematically illustrates an example of a correspondence relation table 11. Here, the correspondence relation table 11 indicates an example of a "correspondence relation" according to the present invention. Further, the correspondence relation storage unit 12 is an example of a "correspondence relation storage unit" according to the present invention. The control unit 2 is then provided with a mixture ratio calculation unit 13 that receives the information from the correspondence relation table 11 stored in the correspondence relation storage unit 12, the flow rate information calculated by the flow rate calculation unit 10, and the information associated with the output from the thermopile 7A, and calculates the mixture ratio of a mixed gas. The mixture ratio calculation unit 13 is an example of a "mixture ratio calculation unit" according to the present invention.

A correspondence table, such as the correspondence relation table 11, may be preliminarily prepared for each flow rate. The correspondence relation table 11 is prepared by plotting the relation between a mixture ratio and an output from the thermopile 7A while a mixed gas consisting of oxygen and nitrogen flows in the flow tube 4 with changes to the mixture ratio. The flow rate is calculated by substituting the difference value between the outputs from the thermopiles 7A, 7B into the expression (1).

Figure 8:
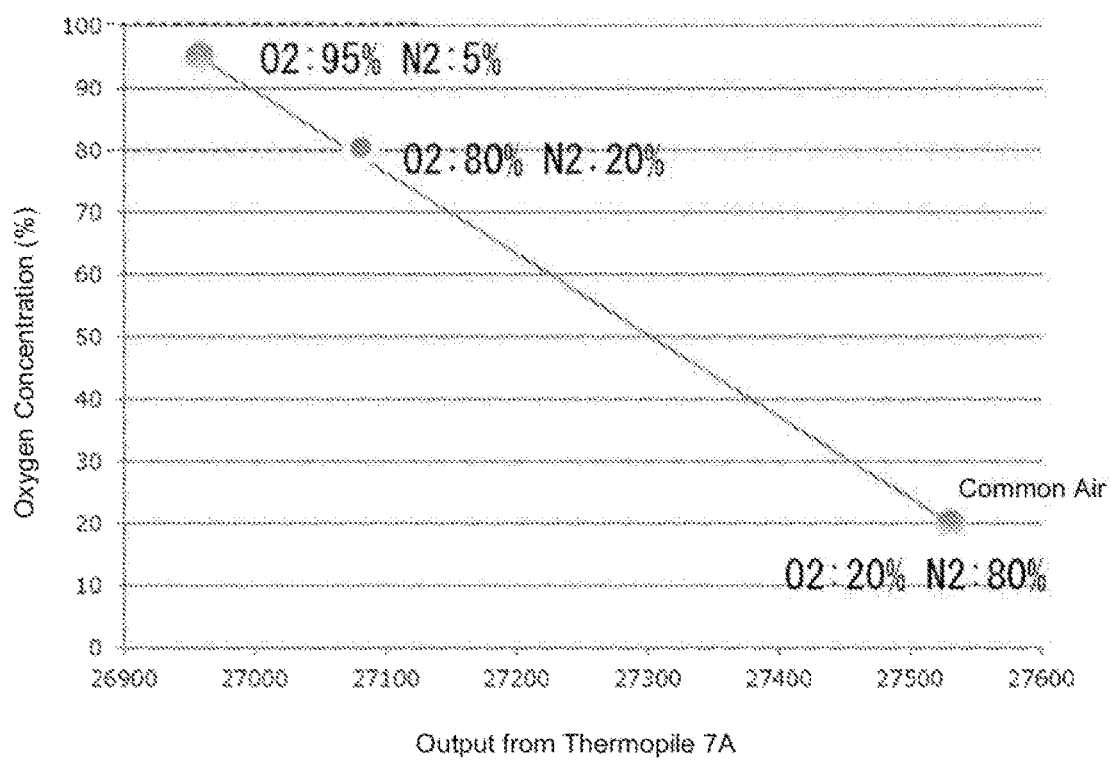
FIG. 8 schematically illustrates an example of the experimental results of plotting the output of one of the thermopiles for a mixed gas with changes to the mixture ratio flowing through the flow tube.

FIG. 8 schematically illustrates an example of the experimental results of plotting the output of the one of the thermopiles (for example, thermopile 7A) for a mixed gas with changes to the mixture ratio flowing through the flow tube 4. As shown in FIG. 8, it can be recognized that outputs from one of the thermopiles correlates with the oxygen concentration. That is, the mixture ratio may be uniquely determined if the output from one of the thermopiles can be obtained.

For a typical mixed gas, the mixture ratio of the mixed gas when creating the correspondence relation table 11 may vary from the mixture ratio of the gas being measured and here, because the extent of thermal diffusivity varies, there is a difference in the outputs from the thermopiles 7A, 7B and in the difference between the outputs from the thermopiles 7A, 7B when creating the correspondence relation table 11 and when measuring a mixed gas, and a difference in the flow rate calculated from the difference between the thermopiles when creating the correspondence relation table 11 and when measuring a mixed gas, even with the same flow rate applied when creating the correspondence relation table 11 and when measuring the gas to be measured. That is, it is difficult to obtain a highly reliable mixture rate even when the correspondence relation table 11 is used to calculate the mixture ratio of the gas being measured.

However, the thermal resistivity, which is an example of a thermal characteristic of oxygen molecules and nitrogen molecules contained in the mixed gas according to the present embodiment is 49192 [s/m$^2$] and 49575 [s/m$^2$] respectively. Given the thermal resistivity, with the same flow rate applied when creating the correspondence relation table 11 and when measuring the gas being measured, there is no difference in the outputs from the thermopiles 7A, 7B and in the difference between the output from the thermopiles 7A, 7B when creating the correspondence relation table 11 and when measuring the mixed gas; and also no difference in the flow rate calculated from the difference when creating the correspondence relation table 11 and when measuring the mixed gas, even when the mixture ratio of the mixed gas when creating the correspondence relation table 11 and the mixture ratio of the gas being measured are different. That is, even if the mixture ratio when creating the correspondence relation table 11 and the mixture ratio of the gas being measured are different, the mixture ratio of the fluid being measured can be calculated using the correspondence relation table 11.

3. Operation Example

Figure 9:
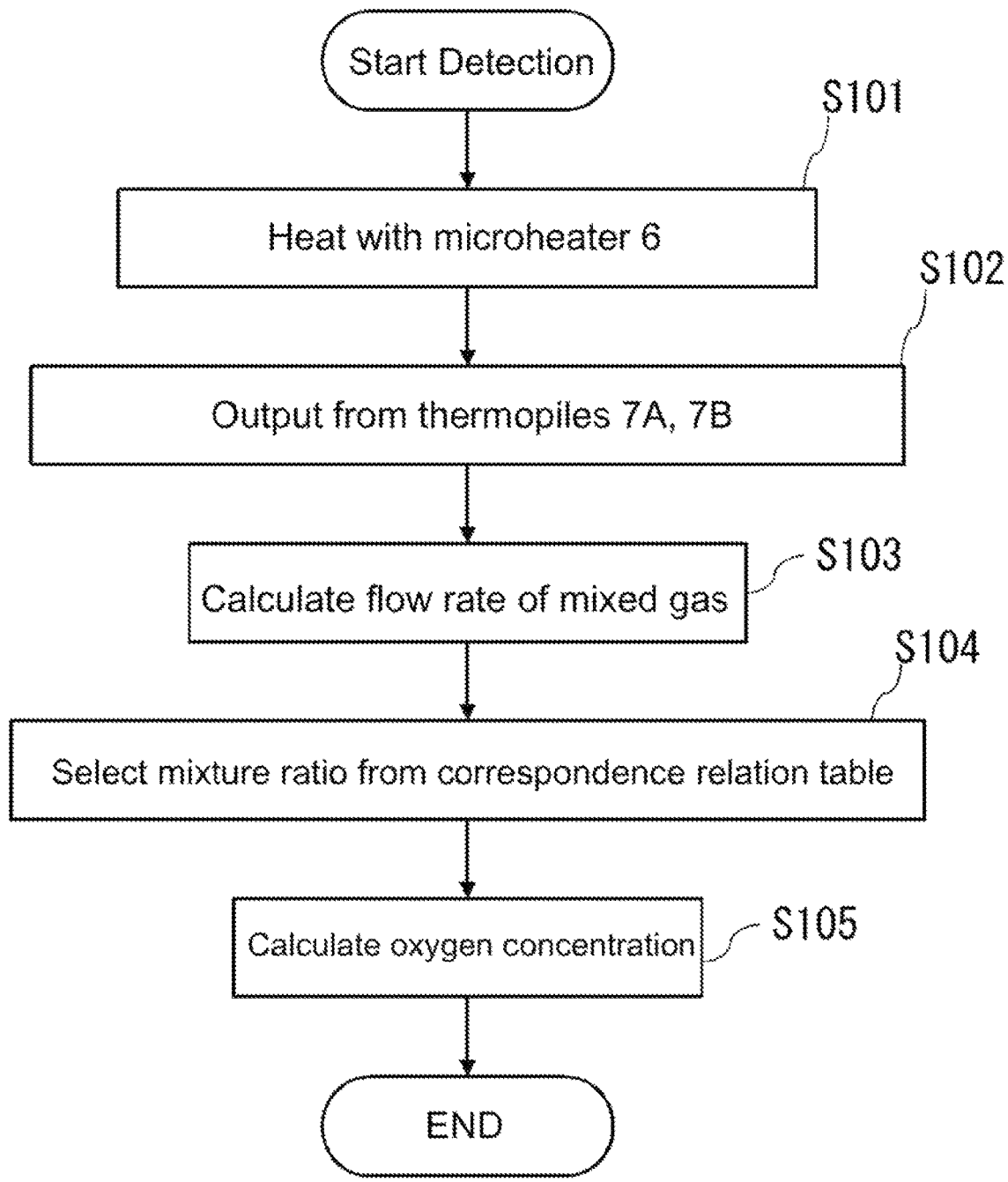
FIG. 9 is a flowchart schematically illustrating an example of a procedure in a detection device according to an embodiment.

Next, the operation example of a detection device 100 is described with reference to FIG. 9; FIG. 9 is a flowchart schematically illustrating an example of a procedure in a detection device 100. The procedure described below is a mere example; each process may be changed as much as possible. Steps can be omitted, replaced, and added as appropriate according to the embodiment in the processing procedure described below.

(Step S101)

First, an oxygen concentrator is used; the microheater 6 is activated when a mixed gas consisting of oxygen and nitrogen is flowing in the flow tube 4. The microheater 6, when activated, heats around the microheater 6.

(Step S102)

In step S102, the thermopiles 7A,7B output signals in accordance with the temperature around the thermopiles. The signals associated with the temperature, which are output from the thermopiles 7A, 7B, are sent to the flow rate calculation unit 10. When the microheater 6 heats its surroundings, the effect of a fluid flowing in the flow tube 4 creates a difference between the output results from the thermopiles 7A, 7B.

(Step S103)

In step S103, the flow rate calculation unit 10 receives signals associated with the temperature output from the thermopiles 7A, 7B and calculates the flow rate of the mixed gas that flows in the flow tube 4 using the expression (1). The flow rate of the mixed gas that flows in the flow tube 4 is calculated in the steps described above. The mixture ratio calculation unit 13 calculates the oxygen concentration of a mixed gas in the following steps using the output from the thermopile 7A, the flow rate of the mixed gas calculated, and the correspondence relation table 11 stored in the correspondence relation storage unit 12.

(Step S104)

In step S104, the flow rate calculated and the mixture ratio corresponding to the output value from the thermopile 7A are selected from the correspondence relation table 11. Here, when selecting the mixture ratio from the correspondence relation table 11, it may be possible to select, from the correspondence relation table 11, the mixture ratios corresponding to the two closest values surrounding the output values from the calculated flow rate and the thermopile 7A so that a value obtained by apportioning these two mixture ratios is used as the mixture ratio of the mixed gas.

(Step S105)

As described above, a mixture ratio is determined by using the output value from the thermopile 7A, the flow rate calculated from the difference between the thermopiles 7A, 7B, and the correspondence relation table 11. An oxygen concentration is then calculated from the calculated flow rate and the mixture ratio. The flow rate and the oxygen concentration of the mixed gas that flows in the flow tube 4 can be obtained by executing the steps described above.

According to the present embodiment, the mixture ratio of a mixed gas is calculated on the basis of the output from the thermopile 7A with reference to the correspondence relation table 11; however, the mixture ratio may also be calculated on the basis of the output from the thermopile 7B. The mixture ratio may be determined by combining the outputs from the thermopiles 7A, 7B. When combining the outputs from the thermopiles 7A, 7B, a highly accurate mixture ratio can be calculated given the amount of information available. The correspondence relation table 11 can be created in advance as appropriate.

[Action and Effect]

As described above, according to the present embodiment, the detection device 100 allows for calculation of the flow rate of a mixed gas consisting of oxygen and nitrogen that flows in the flow tube 4 in an oxygen concentrator. The oxygen concentration in a mixed gas can be obtained on the basis of the flow rate calculated and the output from the thermopile 7A. A mixed gas may contain an increased amount of nitrogen due to the aging of the oxygen concentrator; however, the detection device 100 according to the present embodiment can be used to detect aging. Further, the flow rate and the oxygen concentration can be calculated using a single detection device 100. Therefore, the present embodiment can reduce the costs required for detection.

4. Modification Examples

While an embodiment of the present invention is described above in detail, all points in the previous description are merely examples of the present invention. It goes without saying that various modifications and variations are possible without departing from the scope of the invention. For instance, the following modifications are possible. Note that constituent elements that are identical to the constituent elements in the above described embodiment are given the same reference numerals and where appropriate, a description of features that are identical to the above embodiment is omitted. The following modifications may be combined as appropriate.

<4.1>

Figure 10:
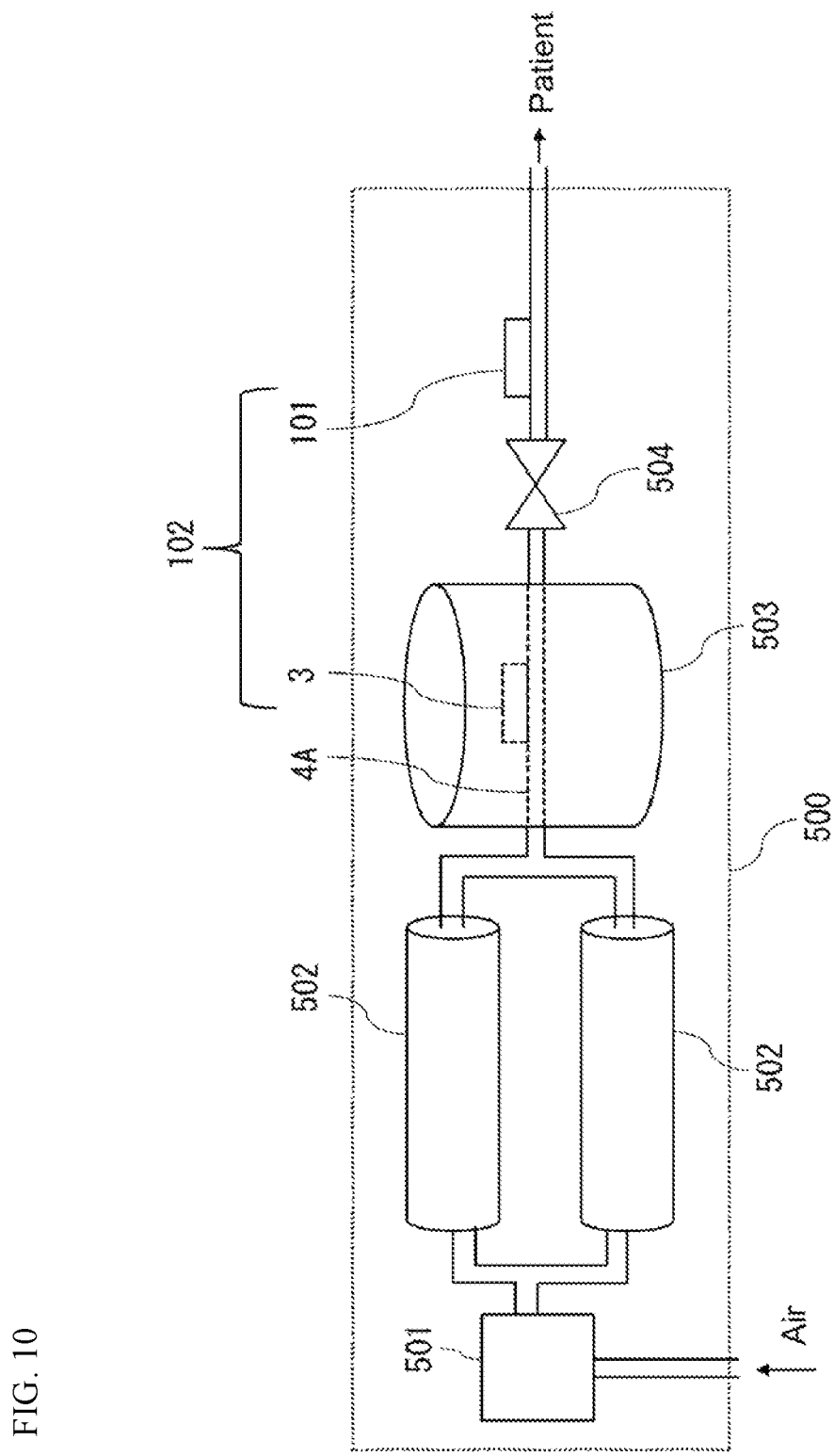
FIG. 10 schematically illustrates an example of a detection device further including a pressure detection device for detecting the pressure of a mixed fluid.

For example, FIG. 10 schematically illustrates an example of a detection device 102 further including a pressure detection device 101 for detecting the pressure of a mixed fluid. Here, the pressure detection device 101 is an example of a "breath detection means" according to the present invention. The detection device 102 can be used to detect, for example, the oxygen concentration of a mixed gas that flows in a flow tube in an oxygen concentrator 500 and the pressure of a mixed gas that flows in the flow tube. The oxygen concentrator 500 is used by, for example, a patient with a respiratory illness. The oxygen concentrator 500 is provided with a compressor 501 for compressing air, for example that is taken from outside the system, and a sieve bed 502 that pressurizes or depressurizes the air compressed by the compressor 501 to thereby create highly concentrated oxygen. The oxygen concentrator 500 is also provided with an oxygen tank 503 for storing the highly concentrated oxygen created, and a flow rate control solenoid valve 504 for controlling the flow rate of the mixed gas that contains the highly concentrated oxygen to be sent from the oxygen tank 503 to a patient.

Here, the circuit board 3 whereon the detection element 1 and the control unit 2 are mounted is provided on a flow tube 4A in the oxygen tank 503. The detection device 102 detects the oxygen flow rate and the oxygen concentration in the flow tube 4A of the oxygen concentrator 500. The pressure detection device 101 is provided partway along the flow tube 4A which extends from the flow rate control solenoid valve 504 to the mouth of a patient. The pressure detection device 101 detects the pressure of the mixed gas consisting of oxygen and nitrogen that passes through the flow tube 4A. Therefore, for example, when a patient with a respiratory illness inhales oxygen from an oxygen concentrator, the pressure detection device may be used to determine whether the patient is breathing normally and to determine the inhalation strength of the patient.

According to the modification example described above, the detection device 102 is provided with the pressure detection device 101, which detects the patient's breathing; however, the detection device 102 may be provided with a flow rate fluctuation calculation unit instead of the pressure detection device 101; the flow rate fluctuation calculation unit calculates the fluctuation in the flow rate of a mixed fluid on the basis of the flow rate of the mixed fluid calculated by the flow rate calculation unit 10. Here, the flow rate fluctuation calculation unit is an example of a "breath detection means" according to the present invention. A detection device 102 thus configured can detect breathing from the flow rate fluctuation calculated by the flow rate fluctuation calculation unit. Further, the configuration allows for breath detection without the need to increase the number of parts, thereby saving cost.

<4.2>

Figure 11:
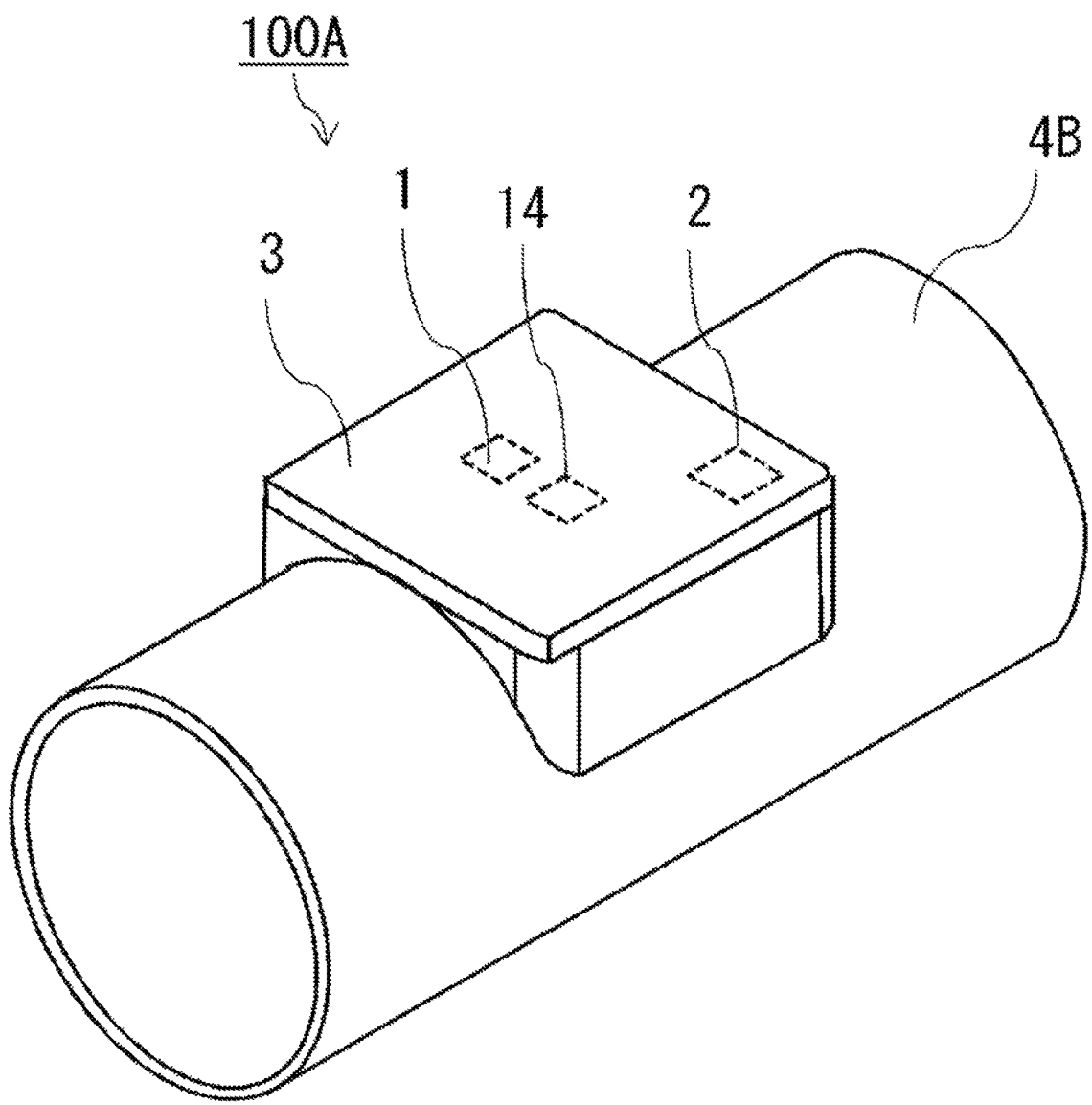
FIG. 11 is a perspective view schematically illustrating an example of a detection device and a flow tube when accounting for the thermal diffusivity of a mixed gas when calculating a flow rate.

When the flow rate calculation unit 10 calculates the flow rate of a mixed gas, the thermal characteristics, such as the thermal diffusivity of the mixed gas, may be considered. This calculation method allows for calculation of a flow rate that is closer to the actual flow rate of the mixed gas. FIG. 11 is a perspective view schematically illustrating an example of a detection device 100A and a flow tube 4B when accounting for the thermal diffusivity of a mixed gas when calculating the flow rate. As shown in FIG. 11, the detection device 100A is provided with a detection element 14 for detecting the thermal diffusivity of the mixed gas in addition to the detection element 1 for measuring the flow rate and the oxygen concentration of the mixed gas and the control unit 2. Further, a flow tube 4B is provided with one flow path section (not shown) like the flow path section 5 of the flow tube 4 along the flow of the mixed gas; the detection element 1 and the detection element 14 are provided side by side along the one flow path section in the direction in which the flow of gas is hindered. The detection element 14 is a thermal flow sensor of the same type as the detection element 1; the detection element 14 is provided with a microheater 6A and thermopiles 7C, 7D as with the detection element 1.

Figure 12:
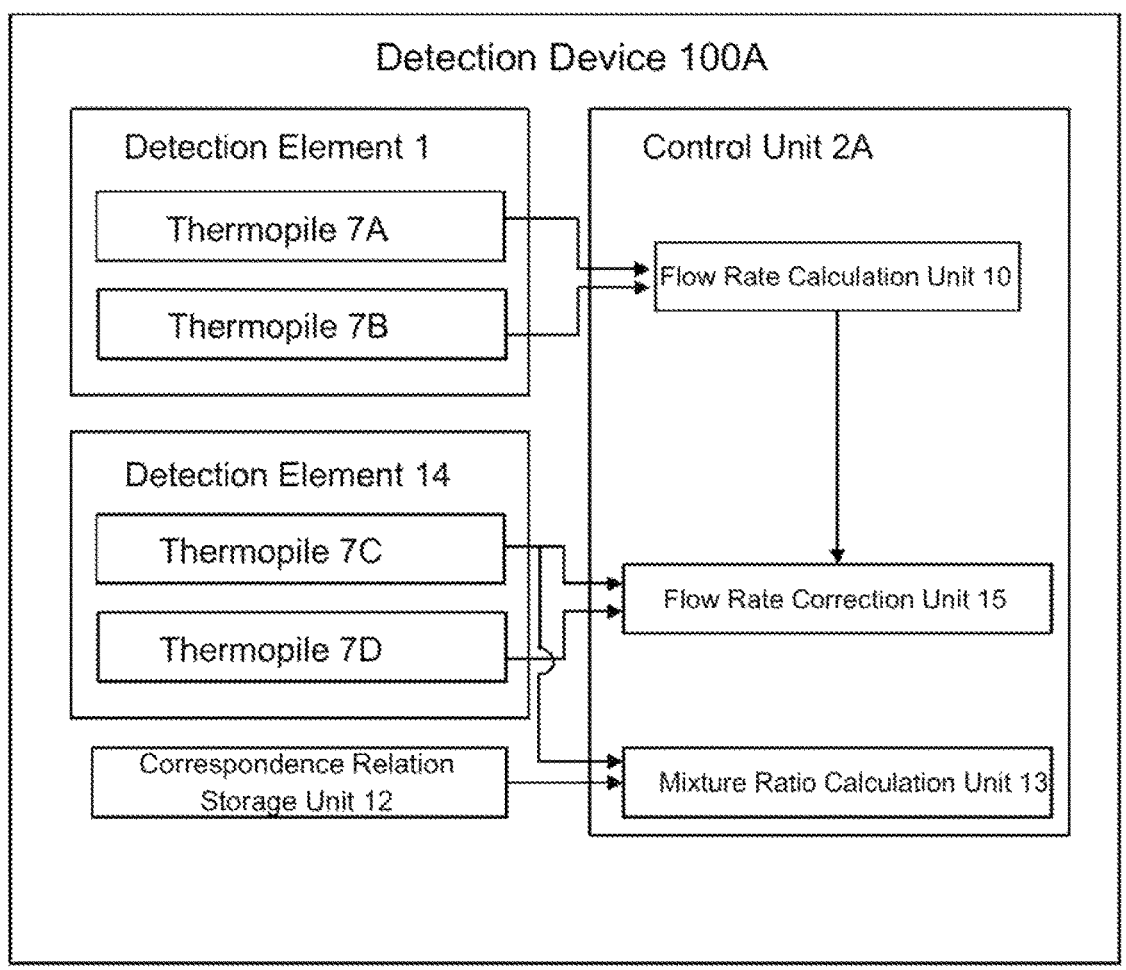
FIG. 12 is a block diagram schematically illustrating an example of a functional configuration of a detection device.

FIG. 12 is a block diagram schematically illustrating an example of the functional configuration of a detection device 100A. A control unit 2A in the detection device 100A is provided with a flow rate correction unit 15 in addition to the configuration of the control unit 2; the flow rate correction unit 15 receives detection results from the thermopiles 7C, 7D of the detection element 14 to correct the flow rate of the mixed gas. The flow rate correction unit 15 is an example of a "flow rate correction unit" according to the present invention. Further, the mixture ratio calculation unit 13 calculates a mixture ratio from the output from the thermopile 7C and the correspondence relation table 11 stored in the correspondence relation storage unit 12. The mixture ratio calculation unit 13 then calculates the oxygen concentration of the mixed gas from the mixture ratio calculated and the flow rate corrected by the flow rate correction unit 15. Here, the correspondence relation table 11 represents the relation between a mixture ratio and an output from the thermopile 7C while a mixed gas consisting of oxygen and nitrogen flows in the flow tube 4B with changes to the mixture ratio.

Figure 13:
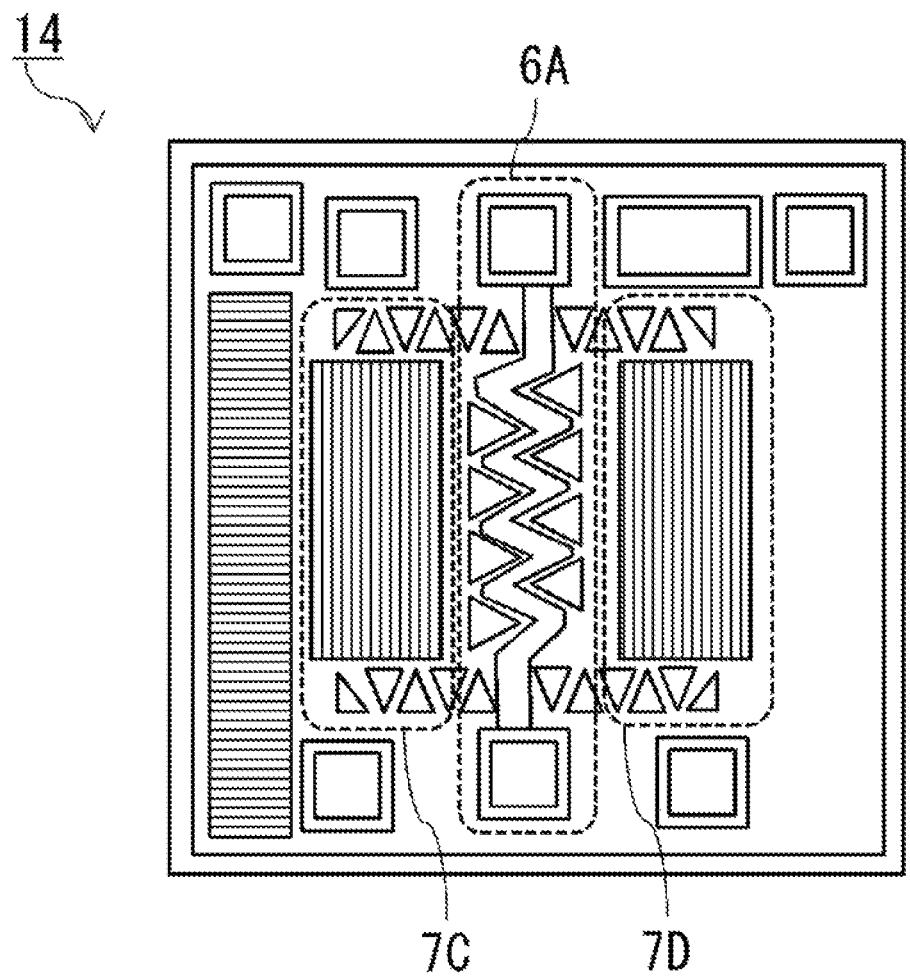
FIG. 13 schematically illustrates an example of the relationship between a detection element and the flow of a mixed gas.
Figure 13:
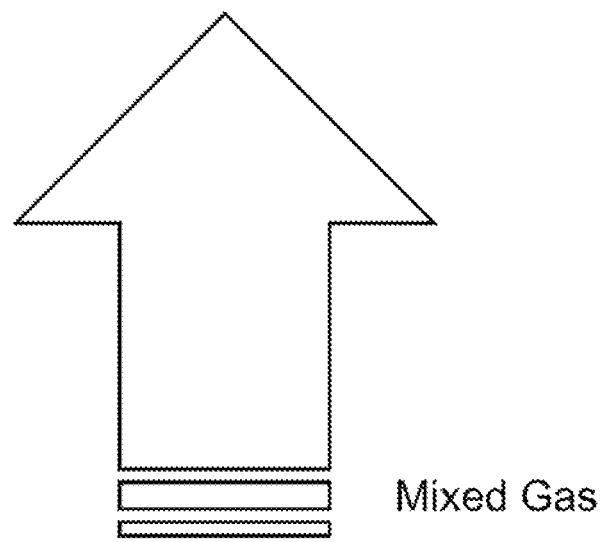

FIG. 13 schematically illustrates an example of the relationship between the detection element 14 and the flow of a mixed gas. The detection element 14 is provided on one flow path section of the flow tube 4B; the microheater 6A and the thermopiles 7C, 7D are arranged side by side in the direction in which the flow of gas is hindered. The thermal diffusivity of the mixed gas can be calculated on the basis of the output from the thermopiles 7C, 7D while the microheater 6A heats the surrounding space. When the microheater 6A and the thermopiles 7C, 7D are arranged side by side in the direction in which the flow of gas is hindered as shown in FIG. 13, the heat from the microheater 6A diffuses symmetrically in both directions toward the thermopiles 7C, 7D with the microheater 6A as the center. The diffusion in both directions toward the thermopiles 7C, 7D is independent of the flow rate. Therefore, the detection element 14 can calculate the thermal diffusivity without relying on the flow rate, on the basis of the outputs from the thermopiles 7C, 7D before and after heating. Furthermore, averaging these two calculated thermal diffusivities can be used to obtain a thermal diffusivity with less of the variation in the output from a thermopile.

The value associated with the thermal diffusivity as calculated above is multiplied by the flow rate of the mixed gas, which was calculated by the flow rate calculation unit 10, to thereby correct the flow rate calculated by the flow rate calculation unit 10 to a flow rate that is closer to the actual flow rate of the mixed gas. Thereby, the present modification example allows for calculation of a value that is closer to the flow rate of a mixed gas that is actually flowing.

The present modification example allows for calculation of a mixture ratio from the output from the thermopile 7C and the correspondence relation table 11. The present modification example allows for calculation of an oxygen concentration from the calculated mixture ratio and the flow rate. Here, the microheater 6A and the thermopile 7C are provided side by side in the direction in which the flow of mixed gas is hindered, and thus the output from the thermopile 7C is independent of the flow rate. That is, a correspondence relation table 11 does not need to be prepared for each flow rate, and flow rate information is not required for calculation of a mixture ratio. That is, the present modification example allows for calculation of a mixture ratio which is not affected by the flow rate, and it can therefore be said that the calculated mixture rate is a highly accurate value.

The present modification example calculates a mixture ratio using the output from the thermopile 7C, however the output from the thermopile 7D may also be used for calculation of the mixture ratio. In this case, the correspondence relation table 11 of outputs from the thermopile 7D and mixture ratios may be prepared in advance. The mixture ratio calculation unit 13 receives the output from the thermopile 7D. A mixture ratio may also be calculated using an average value of the outputs from the thermopile 7C, 7D. In this case, the correspondence relation table 11 between average values of the outputs from the thermopiles 7C, 7D and mixture ratios is prepared in advance. Further, in this case, the mixture ratio calculation unit 13 receives the outputs from the thermopiles 7C, 7D, averages the output values, and uses the averaged values for the calculation of mixture ratios. When a mixture ratio is calculated using the average value of the outputs from the thermopiles 7C, 7D as described above, the effect of variations in output from the thermopiles is reduced, increasing the accuracy of the mixture ratio calculated.

<4.3>

Figure 14:
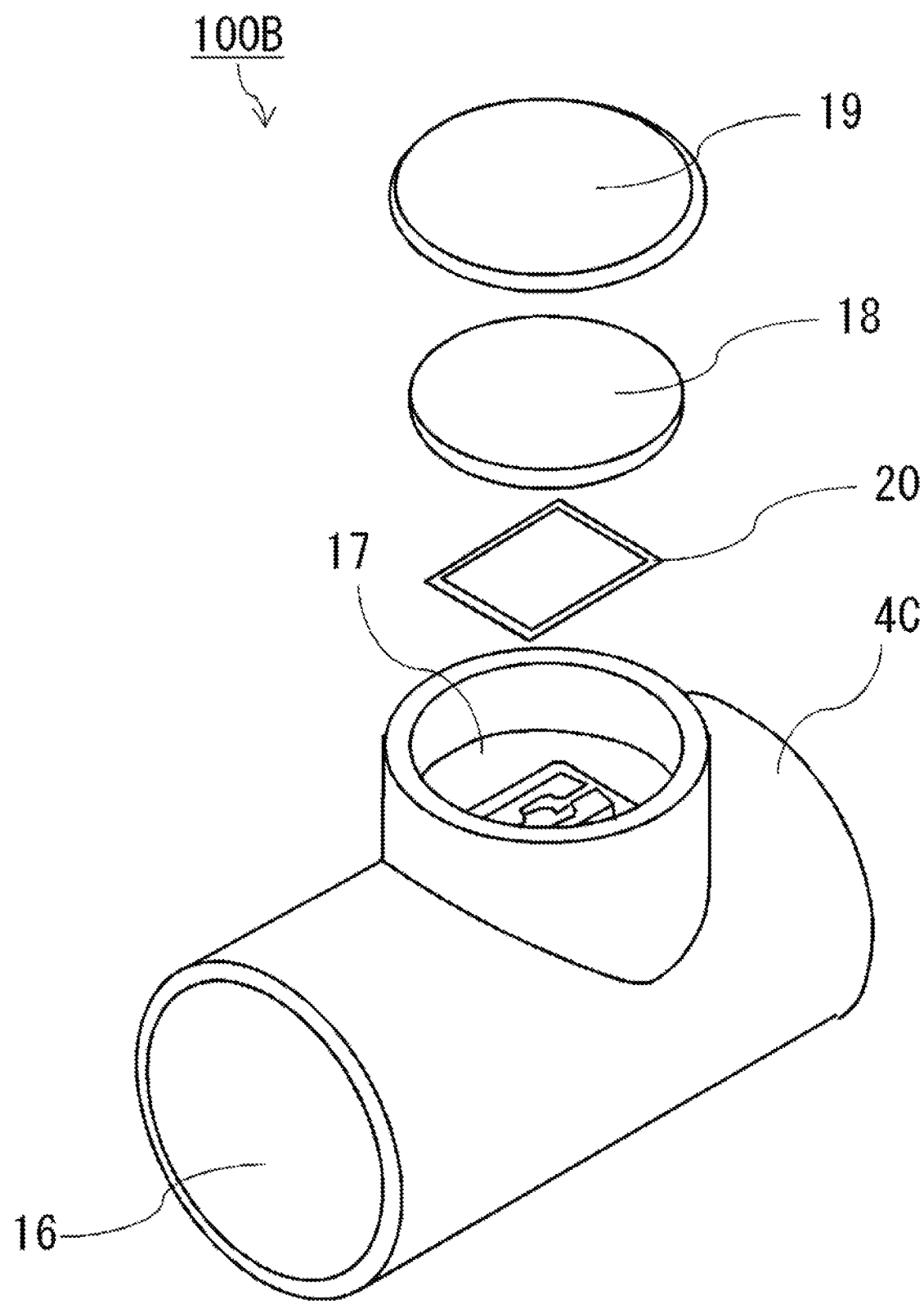
FIG. 14 schematically illustrates an example of mounting a detection device on a flow tube equipped with two flow path sections, i.e., a main flow path section and a sub-flow path section.

The modification example described in <4.2> has the detection element 1 and the detection element 14 in one flow path section of the flow tube 4B, but the detection element 1 and the detection element 14 may be provided on separate flow path sections. FIG. 14 schematically illustrates an example of mounting a detection device 100B on a flow tube 4C equipped with two flow path sections, i.e., a main flow path section 16 and a sub-flow path section 17.

Figure 15:
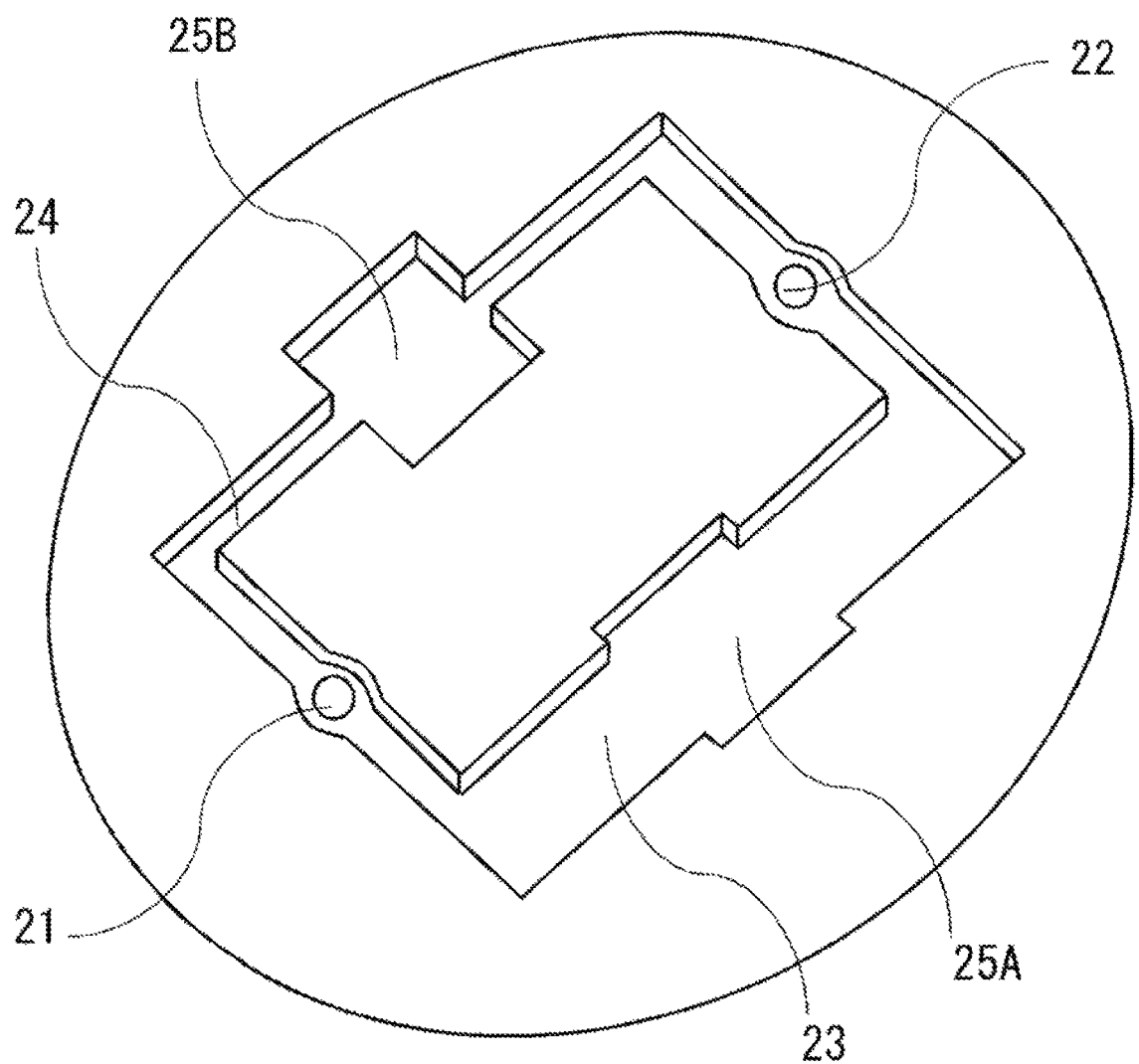
FIG. 15 is a partially enlarged view schematically illustrating an example of a sub-flow path section.

Here, a detection device 100B is provided with a disc-shaped circuit board 18, a cover 19 that covers the outer surface of the circuit board 18, and a seal 20 that sticks the circuit board 18 and the flow tube 4C together. The flow tube 4C is provided with two flow tubes, i.e., the main flow path section 16 and the sub-flow path section 17. The main flow path section 16 is made up of a tube-shaped material. The sub-flow path section 17 is located on the side of the main flow path section 16 and has a sub-flow path therein. FIG. 15 schematically illustrates an example of a partially enlarged view of a sub-flow path section 17. The main flow path section 16 and the sub-flow path section 17 communicate with each other through an inflow path 21 and an outflow path 22. The sub-flow path section 17 is provided with a flow rate detection path 23 that branches off from the inflow path 21 for detecting the flow rate of the mixed gas and a physical property detection path 24 that also branches off from the inflow path 21 to detect the thermal diffusivity of the mixed gas. Further, the flow rate detection path 23 and the physical property detection path 24, which branch off from the inflow path 21, merge to form an outflow path 22.

The flow rate detection path 23 is roughly U-shaped. The flow rate detection path 23 has a detection element mounting section 25A whereon the detection element 1 for detecting the flow rate of the mixed gas is mounted; the detection element mounting section 25A is located partway along the longitudinal direction (i.e., in a direction parallel to the main flow path section 16).

The physical property detection path 24 is also roughly U-shaped as with the flow rate detection path 23. The physical property detection path 24 has a detection element mounting section 25B whereon the detection element 14 for measuring the thermal diffusivity of the mixed gas is mounted; the detection element mounting section 25B is located partway along the longitudinal direction (i.e., in a direction parallel to the main flow path section 16). Here, the microheater and the thermopile of the detection element 14, although not shown here, are arranged side by side in the direction in which the flow of mixed gas is hindered.

According to the present modification example, the length of the main flow path section 16 is approximately 50 mm in the axial direction; the diameter of the inner peripheral surface (the inner diameter of the main flow path section 16) is approximately 20 mm; and the outer diameter of the main flow path section 16 is approximately 24 mm.

A method of securing the detection device 100B to the flow tube 4C is described blow. First, the seal 20 adheres the sub-flow path section 17 and the circuit board 18 together. The surface of the circuit board 18 is then covered with the cover 19. A securing method thus conducted ensures that inside the sub-flow section 17 is airtight. Therefore, air outside the flow tube 4C is prevented from entering the sub-flow path section 17, and thereby prevented from affecting the detection of the flow rate and the physical property.

Figure 16:
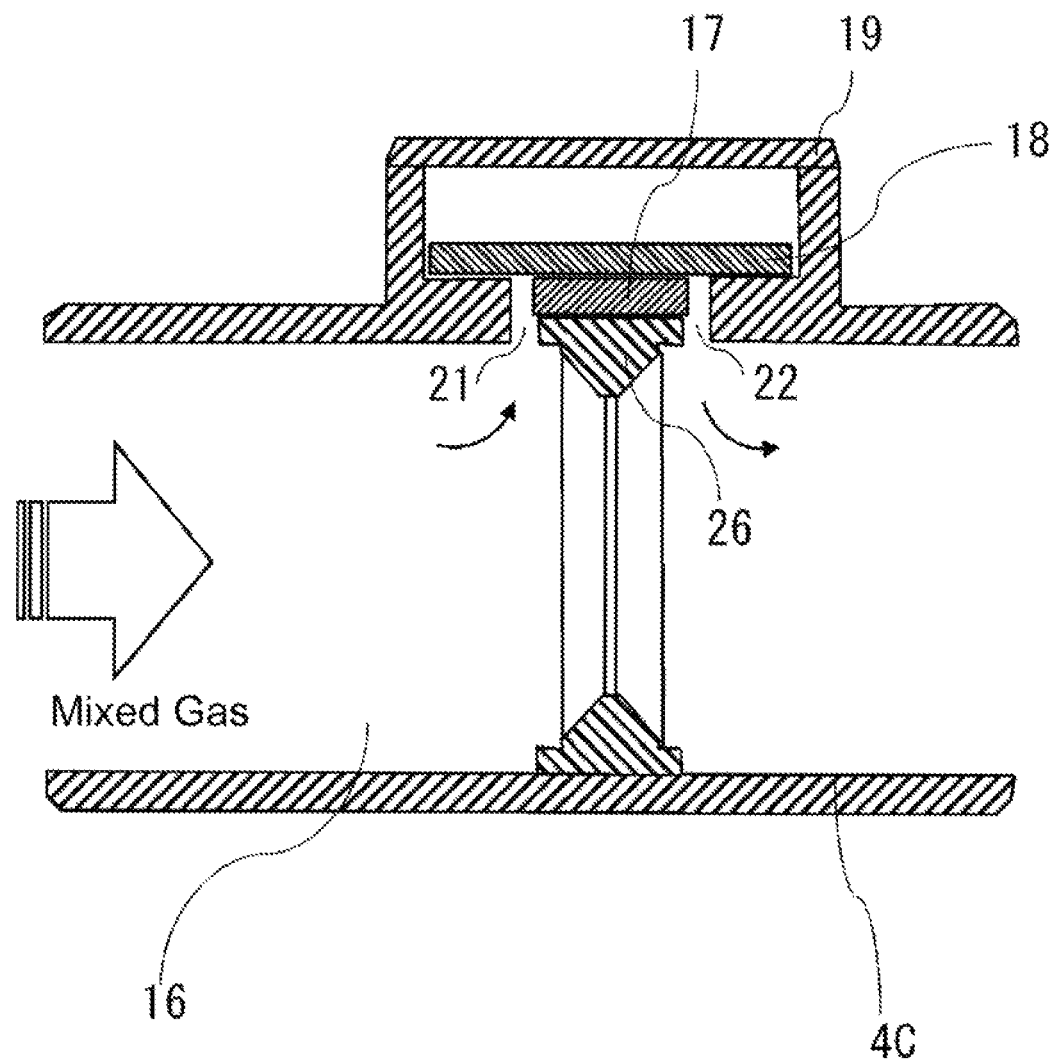
FIG. 16 is a cross-sectional view schematically illustrating an example of when a detection device is provided on a flow tube.

FIG. 16 is a cross-sectional view schematically illustrating an example of when the detection device 100B is provided on the flow tube 4C. The flow tube 4C is provided with a resistor 26 near the sub-flow path section 17. When a mixed gas flows in the main flow path section 16, the resistor 26 obstructs the flow of the mixed gas so that a portion of the mixed gas flows through the inflow path 21 to the sub-flow section 17. Then, a mixed gas under the same conditions of temperature and concentration flows through the flow rate detection path 23 and the physical property detection path 24 which branch off from the sub-flow path section 17. Therefore, it is possible to use the detection element 14 to calculate the thermal diffusivity of a fluid that is under the same conditions of temperature and concentration as the mixed gas detected by the detection element 1. The detection device 100B can thus correct the flow rate of the mixed gas using the thermal diffusivity of a fluid under the same conditions of temperature and concentration, thereby improving the measurement accuracy.

Further, the detection device 100B may adjust the width of the flow rate detection path 23 and the physical property detection path 24 respectively, to thereby separately control the flow rate of gases flowing into the flow rate detection path 23 and the physical property detection path 24. Therefore, the detection device 100B can control the flow rate of a gas flowing in the flow rate detection path 23 in accordance with the detection range of the detection element 1 and can control the flow rate of a gas flowing in the physical property detection path 24 in accordance with the detection range of the detection element 14.

Therefore, the detection device 100B can detect the flow rate and the properties of the gas with a flow rate that is optimal in accordance with the specific detection range of each detection element. The detection elements 1, 14 can thus perform highly accurate measurement of the flow rate and properties of a gas.

It goes without saying that an oxygen concentration can also be calculated from the flow rate obtained as with the modification example <4.2>.

The detection device 100A and the detection device 100B as described above use thermal diffusivity to correct the flow rate; however, a method for correcting the flow rate is not limited to the use of the thermal diffusivity; a detection device may measure a physical property that represents the thermal property of a mixed gas to thus correct the flow rate using the physical property.

According to the embodiment as described above, the correspondence relation table 11 is prepared by plotting the relation between the outputs from a thermopile and the mixture ratios of a mixed gas; however, the relation between a physical quantity correlating to the output from a thermopile and a mixed gas may be plotted to calculate a mixture ratio. Further, according to the detection devices 100A, 100B, the mixed gas consists of oxygen and nitrogen; however, the substances contained in the mixed gas are not limited to oxygen and nitrogen, and the thermal characteristics do not need to be close to each other between substances. The mixture ratio calculation unit 13 is not affected by a flow rate, and the mixture ratio can be estimated using a correspondence relation table that does not rely on a flow rate, as long as a mixed air is always self-evident, so that the flow rate can be corrected on the basis of the estimation results. The substance to be detected is not limited to a gas, and any substance can be detected as long as the substance can flow like a liquid.

According to the detection devices 100A, 100B as described above, the flow rate is corrected by the flow rate correction unit 15, however the flow rate does not have to be corrected.

The embodiments and modification examples as described above may be combined with each other.

Additionally, to facilitate comparison between the configuration requirements of the present invention and the configuration of embodiments, the configuration requirements of the present invention are described with reference numerals.

Embodiment 1

A detection device (100) for detecting the characteristics of a mixed fluid containing different types of substances with different thermal properties within a prescribed range,
the detection device including one or a plurality of heaters (6) for heating the mixed fluid;
a plurality of temperature detectors (7A, 7B, 7C, 7D) for detecting the temperature of the mixed fluid heated;
a flow rate calculation unit (10) for calculating the flow rate of the mixed fluid using the output from at least a portion of the plurality of temperature detectors (7A, 7B, 7C, 7D), the flow rate calculation unit including the heater (6) and at least a portion of the plurality of temperature detectors (7A, 7B, 7C, 7D);
a correspondence relation storage unit (12) that stores the correspondence relation between the output from the temperature detectors (7A, 7B, 7C, 7D) for a prescribed flow rate and the mixture ratio of the substances in the mixed fluid; and
a mixture ratio calculation unit (13) for calculating the mixture ratio of the substances in the mixed fluid on the basis of the output from the temperature detectors (7A, 7B, 7C, 7D) and the correspondence relation.

Embodiment 2

The detection device (100) according to embodiment 1, wherein the mixture ratio calculation unit (13) calculates the mixture ratio of the substances in the mixed fluid on the basis of the outputs from the temperature detectors (7A, 7B) that constitute the flow rate calculation unit (10) and the correspondence relation.

Embodiment 3

The detection device (100A, 100B) according to embodiment 1, wherein the detection device uses the output from the temperature detectors (7C, 7D) which do not constitute the flow rate calculation unit (10) in the plurality of temperature detectors (7A, 7B, 7C, 7D) and are provided side by side in a direction different from the direction in which the mixed fluid flows to thus calculate the physical properties of the mixed fluid; and the mixture ratio calculation unit (13) calculates the mixture ratio of the substances in the mixed fluid on the basis of the outputs from the temperature detectors (7C, 7D) used to calculate the physical properties and the correspondence relation.

Embodiment 4

The detection device (100A, 100B) according to embodiment 3, wherein the detection device is further provided with a flow rate correction unit (15) for correcting the flow rate of the mixed fluid on the basis of the outputs from the temperature detectors (7C, 7D) used to calculate the physical properties.

Embodiment 5

The detection device (100, 100A, 100B) according to any one of embodiments 1 to 4, wherein the different types of substances are oxygen and nitrogen.

Embodiment 6

The detection device (102) according to any one of embodiments 1 to 5, wherein the detection device is further provided with a breath detection means.

Embodiment 7

The detection device (102) according to embodiment 6, wherein the breath detection means is provided with a pressure detection device (101) for detecting the pressure of the mixed fluid.

Embodiment 8

The detection device (102) according to embodiment 6, wherein the breath detection means is provided with a flow rate fluctuation calculation unit for calculating the fluctuation in the flow rate of the mixed fluid on the basis of the flow rate of the mixed fluid calculated by the flow rate calculation unit (10).

REFERENCE NUMERALS

1,14 Detection element
2,2A Control unit 3, 18 Circuit board
4, 4A, 4B, 4C Flow tube
5 Flow path section
6, 6A Microheater
7, 7A, 7B, 7C, 7D Thermopile
8 Insulating thin film
9 Cavity
10 Flow rate calculation unit
11 Correspondence relation table
12 Correspondence relation storage unit
13 Mixture ratio calculation unit
15 Flow rate correction unit
16 Main flow path section
17 Sub-flow path section
19 Cover
20 Seal
21 Inflow path section
22 Outflow path section
23 Flow rate detection path
24 Physical property detection path
25A Detection element placement section
25B Detection element placement section
26 Resistor
100, 100A, 100B, 102 Detection device
101 Pressure detection device
500 Oxygen concentrator
501 Compressor
502 Sieve bed
503 Oxygen tank
504 Flow rate control solenoid valve

The invention claimed is:

1. A detection device for detecting the characteristics of a mixed fluid containing different types of substances with different thermal properties within a prescribed range, the detection device comprising:
   one or a plurality of heaters for heating the mixed fluid;
   a plurality of temperature detectors for detecting the temperature of the mixed fluid heated;
   a memory storing a correspondence relation between a prescribed flow rate and the mixture ratio of the substances in the mixed fluid; and
   a processor or logic configured to perform operations comprising:
   calculating a flow rate of the mixed fluid using the output from a first one or ones of the plurality of temperature detectors on a first flow path, the flow rate calculation unit comprising the heater and the first one or ones of the plurality of temperature detectors;
   selecting from the memory, the correspondence relation between the output from the plurality of temperature detectors for the calculated flow rate and the mixture ratio of the substances in the mixed fluid; and
   calculating the mixture ratio of the substances in the mixed fluid on the basis of the output from the first one or ones of the plurality of temperature detectors and the correspondence relation, wherein the processor or logic is configured to perform operations:
      further comprising calculating physical properties of the mixed fluid using the output from a second one or ones of the plurality of temperature detectors not used for the flow rate calculation and which are provided on a different flow path from the first flow path on which the first one or ones of the plurality of temperature detectors are provided, the second one or ones of the plurality of temperature detectors not used for the flow rate calculation provided side by side in a direction different from the direction in which the mixed fluid flows; and
      such that calculating the mixture ratio comprises calculating the mixture ratio of the substances in the mixed fluid on the basis of the outputs from the second one or ones of the plurality of temperature detectors used to calculate the physical properties and the correspondence relation.

2. The detection device according to claim 1, wherein the processor or logic is configured to perform operations such that calculating the mixture ratio comprises calculating the mixture ratio of the substances in the mixed fluid further on the basis of the output from the first one or ones of the plurality of temperature detectors and the correspondence relation.

3. The detection device according to claim 2, wherein the different types of substances are oxygen and nitrogen.

4. The detection device according to claim 2, further comprising: a breath detection means.

5. The detection device according to claim 4, wherein the breath detection means comprises a pressure detection device for detecting the pressure of the mixed fluid.

6. The detection device according to claim 4, wherein the breath detection means comprises a processor or logic configured to perform operations comprising calculating the fluctuation in the flow rate of the mixed fluid on the basis of the calculated flow rate of the mixed fluid.

7. The detection device according to claim 1, wherein the processor or logic is configured to perform operations further comprising: correcting the flow rate of the mixed fluid on the basis of the outputs from the second one or ones of the plurality of temperature detectors used to calculate the physical properties.

8. The detection device according to claim 7, wherein the different types of substances are oxygen and nitrogen.

9. The detection device according to claim 7, further comprising: a breath detection means.

10. The detection device according to claim 9, wherein the breath detection means comprises a pressure detection device for detecting the pressure of the mixed fluid.

11. The detection device according to claim 9, wherein the breath detection means comprises a processor or logic configured to perform operations comprising calculating the fluctuation in the flow rate of the mixed fluid on the basis of the calculated flow rate of the mixed fluid.

12. The detection device according to claim 1, wherein the different types of substances are oxygen and nitrogen.

13. The detection device according to claim 12, further comprising: a breath detection means.

14. The detection device according to claim 13, wherein the breath detection means comprises a pressure detection device for detecting the pressure of the mixed fluid.

15. The detection device according to claim 13, wherein the breath detection means comprises a processor or logic configured to perform operations comprising for calculating the fluctuation in the flow rate of the mixed fluid on the basis of the calculated flow rate of the mixed fluid.

16. The detection device according to claim 1, further comprising: a breath detection means.

17. The detection device according to claim 16, wherein the breath detection means comprises a pressure detection device for detecting the pressure of the mixed fluid.

18. The detection device according to claim 16, wherein the breath detection means comprises a processor or logic configured to perform operations comprising calculating the fluctuation in the flow rate of the mixed fluid on the basis of the calculated flow rate of the mixed fluid.

* * * * *